(12) United States Patent
Rego et al.

(10) Patent No.: US 11,815,478 B2
(45) Date of Patent: Nov. 14, 2023

(54) THROUGH-TUBING, CASED-HOLE SEALED MATERIAL DENSITY EVALUATION USING GAMMA RAY MEASUREMENTS

(71) Applicant: Halliburton Energy Services, Inc., Houston, TX (US)

(72) Inventors: Pablo Vieira Rego, Rio de Janeiro (BR); Jeffrey James Crawford, Katy, TX (US); Randolph S. Coles, New Caney, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 124 days.

(21) Appl. No.: 17/303,070

(22) Filed: May 19, 2021

(65) Prior Publication Data
US 2022/0373484 A1 Nov. 24, 2022

(51) Int. Cl.
*G01N 23/2206* (2018.01)
*E21B 47/005* (2012.01)
(Continued)

(52) U.S. Cl.
CPC ....... *G01N 23/2206* (2013.01); *E21B 47/005* (2020.05); *G01B 15/00* (2013.01);
(Continued)

(58) Field of Classification Search
CPC .... G01N 9/00; G01N 23/2206; G01N 33/383; E21B 33/14; E21B 47/005
See application file for complete search history.

(56) References Cited

U.S. PATENT DOCUMENTS

| 4,297,575 A | 10/1981 | Smith, Jr. et al. |
| 4,558,220 A * | 12/1985 | Evans ................ G01V 5/125 |
| | | 250/269.3 |

(Continued)

FOREIGN PATENT DOCUMENTS

| BR | 112012019111 A2 | 9/2016 |
| WO | 2015102587 | 7/2015 |

(Continued)

OTHER PUBLICATIONS

Hu et al. "Behind-Casing Cement Void Volumetric Evaluation," SPE-178447-MS (Year: 2015).*
(Continued)

*Primary Examiner* — John Fitzgerald
(74) *Attorney, Agent, or Firm* — DELIZIO, PEACOCK, LEWIN & GUERRA

(57) ABSTRACT

Through-tubing, cased-hole sealed material density can be evaluated using gamma ray measurements. Density evaluation comprises detecting, by at least one detector positioned within a casing of a wellbore including a sealing material positioned between the casing and a subsurface formation, electromagnetic radiation generated in response to nuclear radiation being emitted outward toward the subsurface formation, determining an electromagnetic radiation count based on the detected electromagnetic radiation, selecting at least one of a first reference material having a density that is less than a density of the sealing material and a second reference material having a density that is greater than the density of the sealing material, adjusting the electromagnetic radiation count based on the density of the at least one of the first reference material and the second reference material, and determining a density of the sealing material based on the adjusted electromagnetic radiation count.

18 Claims, 6 Drawing Sheets

(51) Int. Cl.
| | |
|---|---|
| *G01N 9/00* | (2006.01) |
| *G01N 33/38* | (2006.01) |
| *G01V 5/10* | (2006.01) |
| *G01V 5/12* | (2006.01) |
| *G01B 15/00* | (2006.01) |
| *G01V 5/04* | (2006.01) |
| *E21B 33/14* | (2006.01) |
| *G01V 5/08* | (2006.01) |
| *E21B 47/00* | (2012.01) |

(52) U.S. Cl.
CPC .............. *G01N 9/00* (2013.01); *G01N 33/383* (2013.01); *G01V 5/04* (2013.01); *G01V 5/10* (2013.01); *G01V 5/101* (2013.01); *G01V 5/125* (2013.01); *E21B 33/14* (2013.01); *E21B 47/00* (2013.01); *G01N 2223/045* (2013.01); *G01N 2223/053* (2013.01); *G01N 2223/071* (2013.01); *G01V 5/08* (2013.01)

(56) References Cited

U.S. PATENT DOCUMENTS

| | | | |
|---|---|---|---|
| 4,814,611 A * | 3/1989 | Moake | G01V 5/12 250/269.3 |
| 5,258,622 A * | 11/1993 | Pratt, Jr. | G01N 33/383 250/390.05 |
| 5,608,215 A | 3/1997 | Evans | |
| 5,627,368 A | 5/1997 | Moake | |
| 5,900,627 A | 5/1999 | Odom et al. | |
| 6,376,838 B1 | 4/2002 | Odom | |
| 6,936,812 B2 | 8/2005 | Odom et al. | |
| 7,117,092 B2 | 10/2006 | Jacobson | |
| 7,294,829 B2 | 11/2007 | Gilchrist | |
| 7,902,496 B2 | 3/2011 | Botto et al. | |
| 8,731,888 B2 | 5/2014 | Yin et al. | |
| 9,057,795 B2 * | 6/2015 | Guo | E21B 47/005 |
| 9,575,206 B2 * | 2/2017 | Guo | C04B 28/02 |
| 9,939,549 B2 | 4/2018 | Miles et al. | |
| 10,677,040 B2 * | 6/2020 | Hu | E21B 47/005 |
| 10,690,802 B2 * | 6/2020 | Stoller | E21B 33/14 |
| 10,731,455 B2 * | 8/2020 | Fox | G01V 1/40 |
| 2006/0243898 A1 | 11/2006 | Gilchrist | |
| 2010/0193676 A1 | 8/2010 | Jocobson et al. | |
| 2010/0204971 A1 | 8/2010 | Yin et al. | |
| 2010/0252724 A1 | 10/2010 | Inanc et al. | |
| 2011/0191030 A1 | 8/2011 | Roberts | |
| 2013/0261974 A1 * | 10/2013 | Stewart | G01V 5/125 250/269.3 |
| 2016/0202387 A1 * | 7/2016 | Fox | G01V 11/002 73/152.58 |
| 2016/0238736 A1 * | 8/2016 | Guo | E21B 47/00 |
| 2018/0172876 A1 * | 6/2018 | Inanc | G01V 5/045 |
| 2018/0210109 A1 * | 7/2018 | Guo | E21B 49/08 |
| 2019/0033484 A1 * | 1/2019 | Stoller | G01V 5/101 |
| 2021/0389495 A1 * | 12/2021 | Millot | E21B 47/12 |

FOREIGN PATENT DOCUMENTS

| | | | |
|---|---|---|---|
| WO | 2016053344 A1 | 4/2016 | |
| WO | WO-2017086973 A1 * | 5/2017 | ......... E21B 47/0005 |

OTHER PUBLICATIONS

Khalifeh et al. "Technology Trends in Cement Job Evaluation Using Logging Tools," SPE-188274-MS (Year: 2017).*

"GB Application No. 2113115.6, Combined Search and Examination Report", dated Apr. 28, 2022, 11 pages.

* cited by examiner

US 11,815,478 B2

1

THROUGH-TUBING, CASED-HOLE SEALED MATERIAL DENSITY EVALUATION USING GAMMA RAY MEASUREMENTS

BACKGROUND

The disclosure generally relates to wellbore logging, and more particularly to cased-hole evaluation using gamma ray measurements.

For hydrocarbon recovery from a wellbore, evaluation of compositional characteristics of the surrounding subsurface formation can be important. For uncased, open wellbores, a conventional approach for such evaluation includes emission and detection of gamma ray radiation. For example, a tool that includes a radiation source or emitter and two or more detectors can be positioned downhole at a location close to the formation. The radiation source can emit neutrons into the subsurface formation. The emitted neutrons can propagate outward from the source into the formation and generate gamma rays. The detectors can then measure the number, or count rate, of backscattered gamma rays that are received at each of the detectors. Energy distribution can occur differently for each detector due to different paths of interaction inside the matter under measurement. The bulk density of the formation can be determined from the counts and the energy distribution.

BRIEF DESCRIPTION OF THE DRAWINGS

Embodiments of the disclosure may be better understood by referencing the accompanying drawings.

DESCRIPTION

Figure 1:
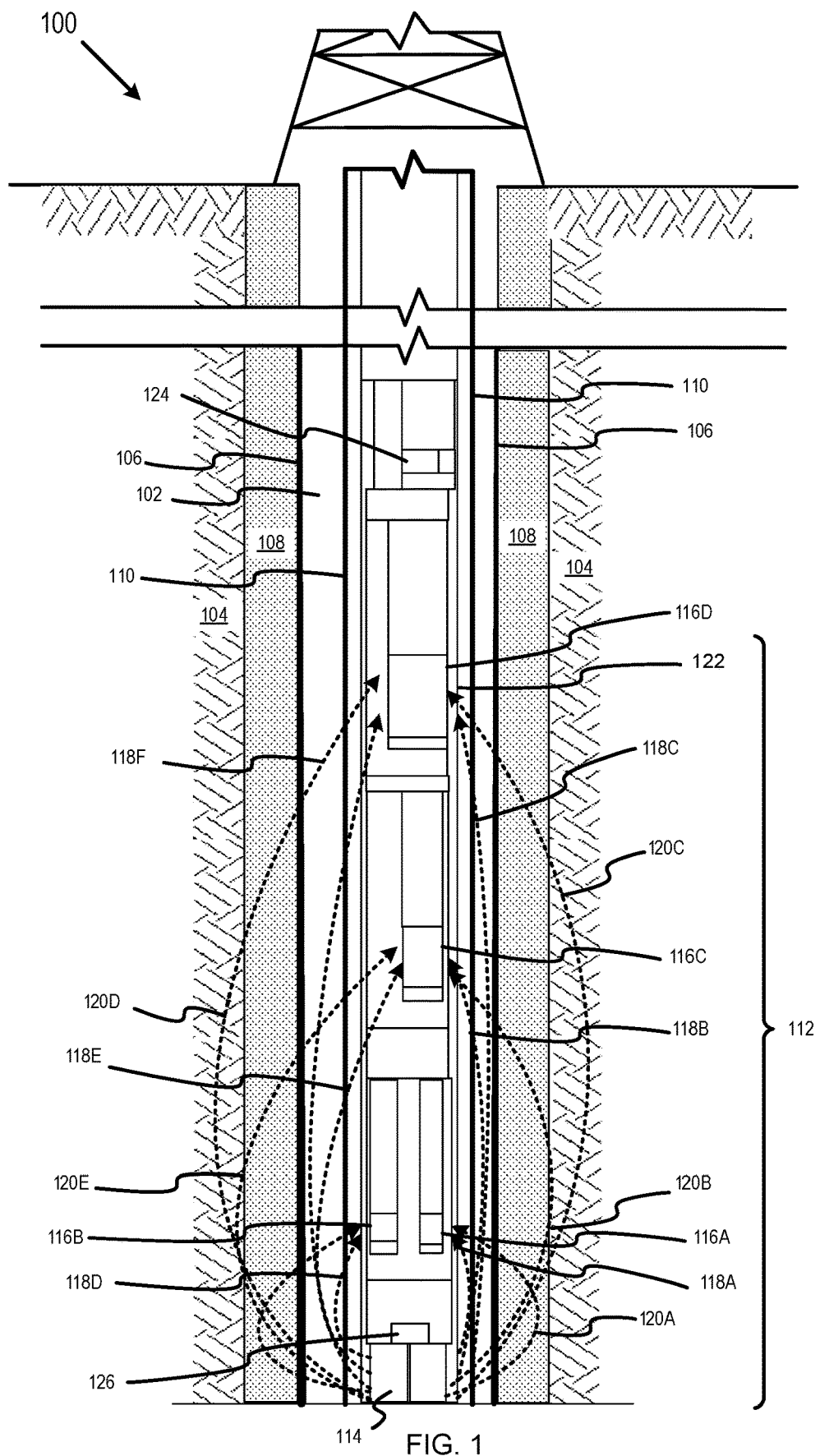
FIG. 1 depicts a side, cut-away view of a cased-hole logging environment with production tubing installed, according to some embodiments.

The description that follows includes example systems, methods, techniques, and program flows that embody aspects of the disclosure. However, it is understood that this disclosure may be practiced without these specific details. For instance, this disclosure refers to density determination in a cased-hole environment in illustrative examples. Aspects of this disclosure can be also applied to density tools in open-hole environments. In other instances, well-known instruction instances, protocols, structures and techniques have not been shown in detail in order not to obfuscate the description.

Example embodiments relate to a density evaluation of cement positioned between a casing of a wellbore and a surrounding subsurface formation based on gamma ray measurements. In some embodiments, the gamma ray tool for emission and detection can be positioned within multiple shielding layers including the casing and a tubing within the casing. In some embodiments, the density evaluation includes using raw counts for an unmodified spectral density tool to calculate the bulk density, which is the apparent density or volumetric density, behind cased-hole formation. Example embodiments can then modify the raw signal counts into a density-like course experimentally determined and calibration. Spectral density tools are typically used for determination of density from a formation in open-hole environment. Example embodiments can extend the applicability of these density tools, since the new cased-hole environment will not restrict the use to determine density behind casing. Accordingly, example embodiments can employ current spectral density tools to perform cement density evaluation.

For a cased-hole environment, a shielding layer (such as a steel alloy) would be positioned between the subsurface formation and a measuring tool. For example, a shielding layer can include a casing of the wellbore and/or a tubing. The measuring tool can, therefore, be positioned within multiple shielding layers relative to the subsurface formation. Typically, the casing is cemented in place to protect the open wellbore from fluids, extreme pressures, wellbore stability problems, etc. The casing is typically much heavier than usual wellbore formation constituents. The heavier casing can absorb a portion of the electromagnetic radiation emitted from the source of the measuring tool. The casing can also backscatter a significant portion of incident radiation to the detectors. This absorption and backscattering of the emitted radiation by the casing can deteriorate measured signals and cause a loss of information related to a sealing material of interest behind the casing, which is typically cement. Accordingly, evaluating a density of this material can include greater error when using conventional density determination operations.

In example embodiments, raw gamma ray counts (hereinafter "counts") for an unmodified spectral density tool can be used to calculate the bulk density of behind cased-hole formation by accounting for the absorption and backscattering resulting from the casing and/or the tubing. Example embodiments can include post-processing of the raw signal counts to generate an experimentally determined density-like value that can be normalized using a benchmarking calibration. In some embodiments, counts can be measured for corresponding energy windows on at least a near and far detector of a bulk or spectral density tool (hereinafter "density tool"). An average subset of points can be generated for each energy window based on the near and far counts. This average subset of points for each energy window can then be normalized according to a density of one or more reference materials. For example, normalization can be based on a first reference material that is heavier than the material behind the casing that is under investigation and a second reference material that is lighter than the material under investigation. A final projected value for the density of the material under investigation can then be obtained using the normalized values for each of the energy windows.

By projecting the density using raw counts, typical density tools usually used for determination of density of a formation in open-hole environment can be used. This method can extend the applicability of the current density tools, since the new cased-hole environment will not restrict the use to determining the density behind casing. This reduces the number of tools needed to be run downhole and saves space and time to maximize asset value. For existing density tools, example embodiment operations can be added as an extending plugin. Such a plugin can enhance the ability of existing density tools to recognize new scenarios of use and still determine the density or the formulation.

Example Application

FIG. 1 depicts a side, cut-away view of a cased-hole logging environment with production tubing installed, according to some embodiments. A logging environment 100 includes a wellbore 102 that has been formed in a subsurface formation (hereinafter "formation") 104. The wellbore 102 has been cased with a casing 106. A sealing material (e.g., cement) 108 has been poured or flowed between the casing 106 and the formation 104. A production tubing 110 is positioned in the wellbore 102 within the casing 106. Also, a density tool 112 is positioned within the production tubing 110. In some embodiments, the density tool 112 is a spectral density tool.

The density tool 112 may include a source 114 and a plurality of gamma ray detectors 116A-D. The source 114 may be a radiation source, such as neutron generator or pulsed neutron generator. Neutrons from the source 114 may travel through the wellbore 102, the production tubing 110, the casing 106, the sealing material 108, and/or the formation 104, generating gamma rays 118A-F and 120A-F in the process. The casing 106 scatters gamma rays 118A-F back into the detectors 116A-D in the density tool 112. Gamma rays 120A-F may pass through the casing 106 into the sealing material 108 and the formation 104. The number of gamma rays 118A-F and 120A-F that reach the detectors 116A-D depends on many factors, one of which is the density of the formation 104. The detectors 116A-D measure the energy of each gamma ray 118A-F and 120A-F and the time at which it is detected. The detected gamma rays can be used to determine the density of the sealing material 108 (as further described below).

The source 114 may comprise a relatively long, thin tube in which deuterium and tritium ions (isotopes of hydrogen) are accelerated in an electric field and focused so as to collide with a target that also contains deuterium and tritium. When deuterium and tritium atoms collide, they produce neutrons with an energy of about 14.1 megaelectron volts (MeV). Neutrons created by the source 114 can propagate in different directions and interact with the matter they encounter. This can produce the gamma rays 118A-F, 120A-F through two different mechanisms (elastic scattering and inelastic scattering). In elastic scattering, a neutron scatters off of a nucleus without changing the structure of the nucleons in the nucleus. No gamma rays are produced, but the neutron loses energy. In inelastic scattering, a neutron scatters off a nucleus and perturbs the structure of the nucleus, leaving it in a higher-energy configuration. However, the nucleus cannot stay in that configuration long. When the nucleus reverts to its original state, one or more inelastic gamma rays can be emitted. In some instances, the gamma rays 118A-F may be inelastic gamma rays. This interaction significantly reduces the energy of the neutron. The neutron eventually reaches an energy where the neutron is in equilibrium with the surrounding temperature as a result of these elastic and inelastic interactions. At this energy, the neutron will bounce around the environment until captured by a nucleus in a process called neutron capture, converting the nucleus to a new isotope. In general, this reaction does not leave the new isotope in its lowest-energy configuration. Thereafter, the new isotope will eventually decay into its lowest-energy configuration, also emitting gamma rays, such as the gamma rays 120A-F, in the process. These gamma rays 120A-F may be called capture gamma rays.

Inelastic scattering occurs when neutrons have a relatively high energy, so these reactions occur within a few microseconds of when the neutron is generated before it has lost too much energy. As a matter of contrast, neutron capture occurs when the neutrons are at a very low energy, perhaps as much as 1000 microseconds after the neutron was generated. Since the gamma rays 118A-F and 120A-F generated by these reactions contain different information about the surrounding environment, it is useful to differentiate between the two types of gamma rays. Towards this end, the source 114 is typically operated as a pulsed generator by turning it on and off in a cyclical fashion. Thus, it is typically on for a short period, called the neutron burst, and off for hundreds or thousands of microseconds.

The gamma ray detectors 116A-D may comprise scintillating crystals attached to photomultipliers. The gamma rays 118A-F and 120A-F scatter off electrons in the crystals, which in turn generate light. Some of the light reaches the photomultiplier, which converts it into an electronic signal. Proper manipulation of this signal provides an electronic pulse whose amplitude is proportional to the energy deposited in the crystal. Various types of crystals can be used, including but not limited to sodium iodide, bismuth germinate, cesium iodide, gadolinium orthosilicate, and lanthanum bromide.

The density tool 112 may include materials with low atomic number between one or more of the detectors 116A-D and the front 122 of the density tool 112 to facilitate low-energy gamma rays reaching the detector 116. This can improve sensitivity to the photoelectric factor, Pe, of the sealing material 108. In some embodiments, the neutron output of the source 114 can be approximately constant but can vary by 50% or more during logging runs due to temperature fluctuations. Because a measured and/or accurate knowledge of the neutron output of the source 114 is not usually available, techniques have been developed to make various measurements independent of the absolute output of the source 114. For example, one mechanism for managing the variability in neutron output is to use ratios of counts in multiple detectors to reduce sensitivity to absolute neutron output with respect to quantities such as the estimated density of the sealing material 108, the formation 104, etc.

In some embodiments, where neutron output can be accurately measured on a substantially continuous basis, some parameters of interest can be computed from a single detector of the detectors 116A-D. Thus, the density tool 112 may include a device 126 that measures the neutron output of the source 114 as a function of time. This device 126 may include a radiation detector or some other measure of neutron output, such as an operational parameter of the source (e.g., generator target current).

Example Data Flow

Figure 2:
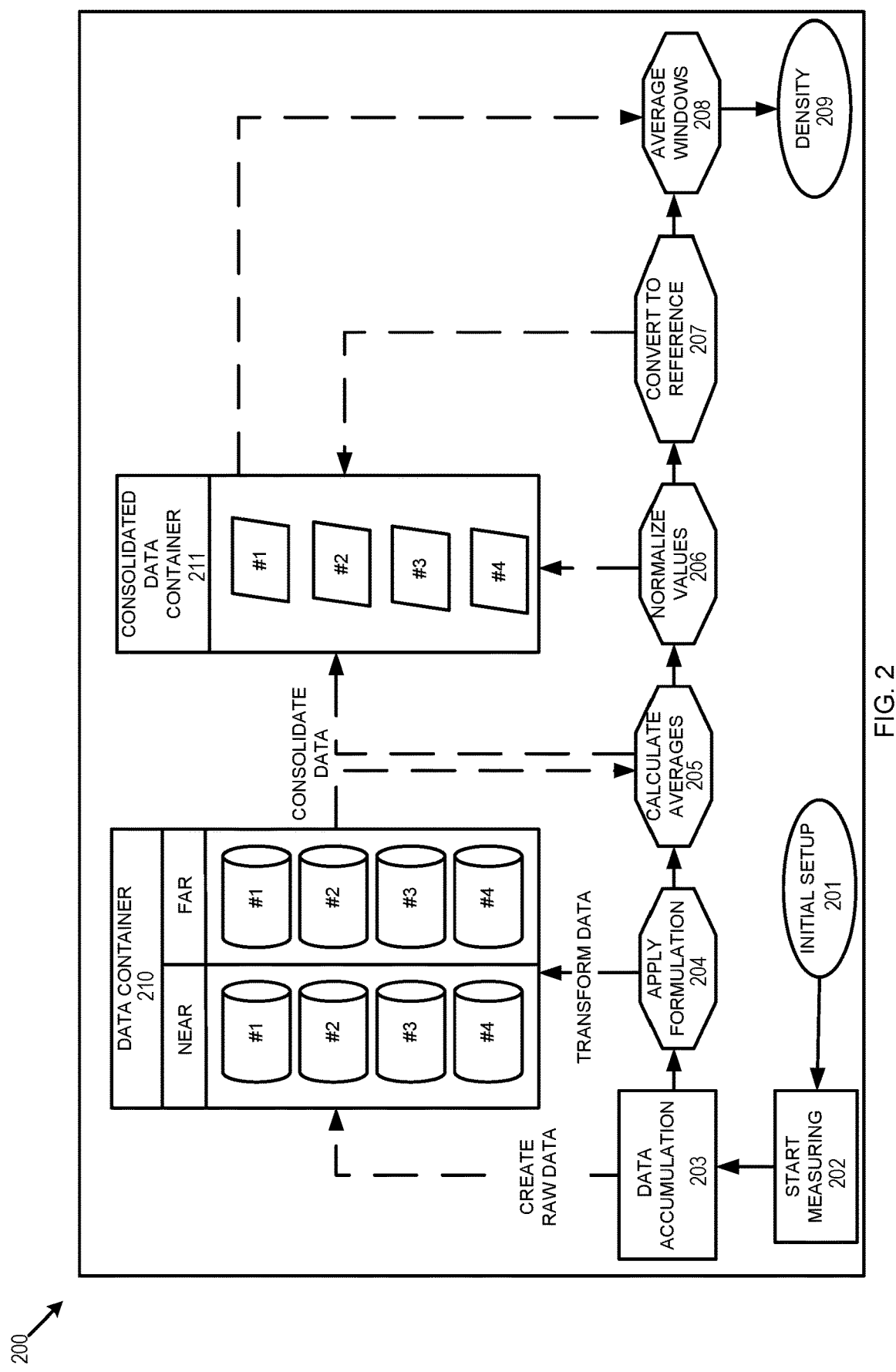
FIG. 2 depicts a data flow diagram for cement density evaluation for a cased wellbore with production tubing installed, according to some embodiments.

FIG. 2 depicts a data flow diagram for through-tubing cement density evaluation, according to some embodiments. A system 200 may be part of a density tool, such as the density tool 112 of FIG. 1, or may be part of a computer on the surface in communication with a density tool downhole. Operations of the system 200 may be implemented using a density calculation software, hereinafter referred to as a "density calculator". Operations of the system 200 may begin with an initial setup 201 of the density tool. The initial setup FF01 may include configuring the measurement software of the density tool. The initial setup FF01 may also include insertion of calibration parameters. The initial setup FF01 may be a real-time calibration process that maps a response of the tool to a standard tool response to prepare for tool operation.

After the initial setup FF01, the density tool starts measuring FF02. Beginning measurements may include emitting neutrons from a source and detecting gamma rays produced from the emitted neutrons at multiple energy windows of a near and far detector of the density tool. For example, the near and far detectors may include four energy windows for measuring raw counts of gamma rays detected by each window. Data accumulation FF03 occurs until a statistically significant amount of data has been gathered. Data accumulation may be dependent upon a time or a number of counts detected. For example, data accumulation FF03 may occur for time intervals of 1, 5, 10, and/or 15 minutes. Alternatively, data accumulation may occur until a predefined number of counts have been detected.

This accumulated data may be stored in a data contained FF10 in the form of raw data created during data accumulation FF03. The data container FF10 may store data according to the detector that measured the data (i.e. the near detector or the far detector) and may further store the data according to the energy window of each detector (i.e. #1 for the lowest energy window, #2 for the second lowest energy window, #3, for the second highest energy window, and #4 for the highest energy window).

To determine through-casing density of a material under investigation, the density calculator applies a formulation FF04 to transform the raw data. Applying the formulation FF04 includes generating a subset of data points for each energy window using the accumulated data of the near and far detectors. The new subsets of data may be sent to the data container FF10 and stored as transformed data.

For each new subset corresponding to each energy window, the density calculator calculates averages FF05. The averages may be determined in real time using the formulated data. The averages may also be determined using data stored in the data container FF10. The averages may be stored in as consolidated data in a consolidated data container FF11. The consolidated data container FF11 may store data from the near and far detector as consolidated data for each energy windows. The density calculator may then normalize the values FF06 according to calibration coefficients. The calibration coefficient may be determined using reference materials related to the mechanical structure of the components in the wellbore and the material under investigation. These normalized values may also be stored in the consolidated data container FF11. The normalized values are converted to a reference density FF07 using reference materials from the calibration process. These reference densities may also be stored in the consolidated data container FF11. Finally, the density calculator averages the windows FF08 to obtain the final projected density FF09.

Example Operations

Figure 3:
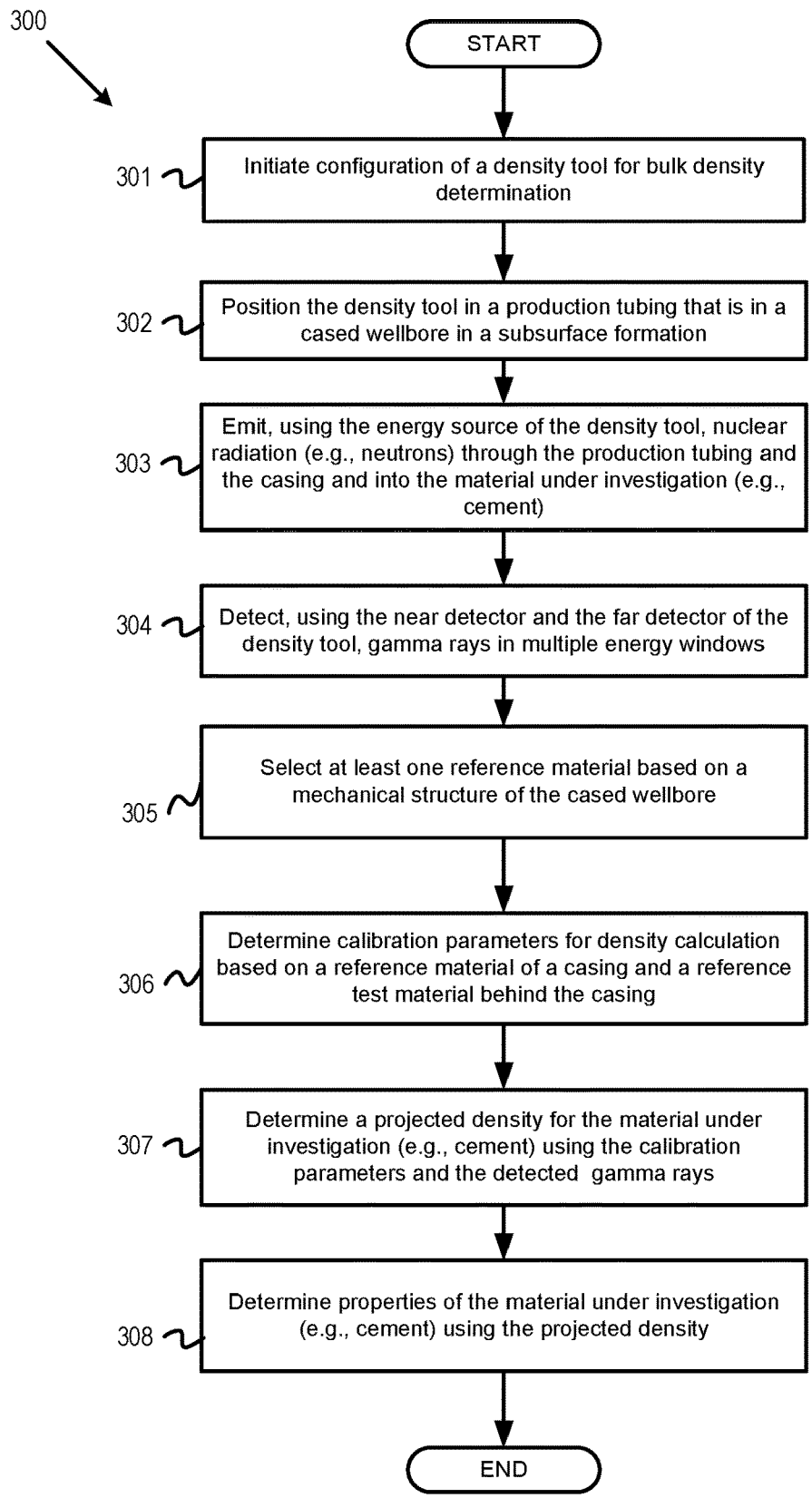
FIG. 3 depicts a flowchart of example operations for cement density evaluation for a cased wellbore with production tubing installed, according to some embodiments.

FIG. 3 depicts a flowchart of example operations for cement density evaluation for a cased wellbore with production tubing installed, according to some embodiments. Operations of a flowchart 300 are described in reference to the system 100 of FIG. 1. Operations of the flowchart 300 can be performed by hardware, software, firmware, or a combination thereof. Operations of the flowchart 300 begin at block 301.

At block 301, a configuration of a density tool is initiated for bulk density determination. For example, with reference to FIG. 1, a computer at the surface of the wellbore 102 can configure the density tool 112. The configuration of the density tool 112 can include a real time set up that defines parameters of operations, such as time for measurement. The initial configuration of the tool maps the response of the tool and/or a sensor package of the tool to a standardized senor. The configuration is a characterization process that averages multiple tools to build an average expected response by mapping the response of any tool in a tool package to a standard.

At block 302, the density tool is positioned in a production tubing of a cased wellbore formed in a subsurface formation. For example, with reference to FIG. 1, the density tool 112 is positioned in the production tubing 110 in the wellbore 102. A neutron source, such as the source 114 of FIG. 1, may be lowered into the wellbore. The configured density tool consists of an energy source and at least two analogous detectors at different fixed positions from the energy source positioned along the tool surface. For example, the energy source may be a cesium 137 gamma source. The source is shielded from the detectors so that only scattered gamma radiation is detected. The detectors are referred to based on their relative distance from the source with a "near detector" being the detector closest to the source and a "far detector" being the detector at a further distance from the source. For example, with reference to FIG. 1, the detector 116A may be a near detector while the detector 116D may be a far detector.

Each detector includes raw energy windows to detect scattered gamma radiation of various energies. The windows are typically arranged in order of lowest energy to highest energy. For example, in a density tool with four raw energy windows, window one would detect the lowest energy radiation while window four would detect the highest energy radiation. The energy windows may be configured and referred to based on their analysis capabilities. For example, there may be a lithology window, a peak window, and a density window. As another example, the windows may be referred to based on the radiation detected such as a cesium window and a barite window. There may be more than one window configured for detection of a given characteristic. While examples may refer to four windows, the number of windows may vary as long as there is at least one low energy window and one high energy window since lower energy windows are more sensitive to photoelectric effects and higher energy windows are more sensitive to an electron density of a material. The detectors are configured to record the number, or count, of scattered radiation particles that hit each raw energy window to measure the amount of scattered radiation in each energy range.

At block 303, the energy source of the density tool emits nuclear radiation (e.g., neutrons) through the production tubing and the casing and into the material under investigation (e.g., cement). For example, with reference to FIG. 1, the source 114 can emit the nuclear radiation through the production tubing 110 and the casing 106 and into the sealing material 108. The source 114 can bombard the sealing material 108 with neutrons to create high energy gamma rays, the attenuation of which can be used to determine the density of subsurface objects (e.g., the sealing material 108).

At block 304, gamma rays are detected in the multiple energy windows of the density tool using the near detector and the far detector. For example, with reference to FIG. 1, one or more of the detectors 116A-116B can be considered the near detector and one or more of the detectors 116C-116D can be considered the far detector. The detectors 116 can measure the number of gamma rays that are accumulated for multiple energy windows. Measurements of the number of gamma rays that are accumulated from raw energy windows can be referred to as counts. Gamma rays can be detected at the multiple energy windows and counts can be accumulated, until a statistically significant number of measurements have been recorded. For example, detection may occur for a set time interval, such as ten minutes.

Figure 4:
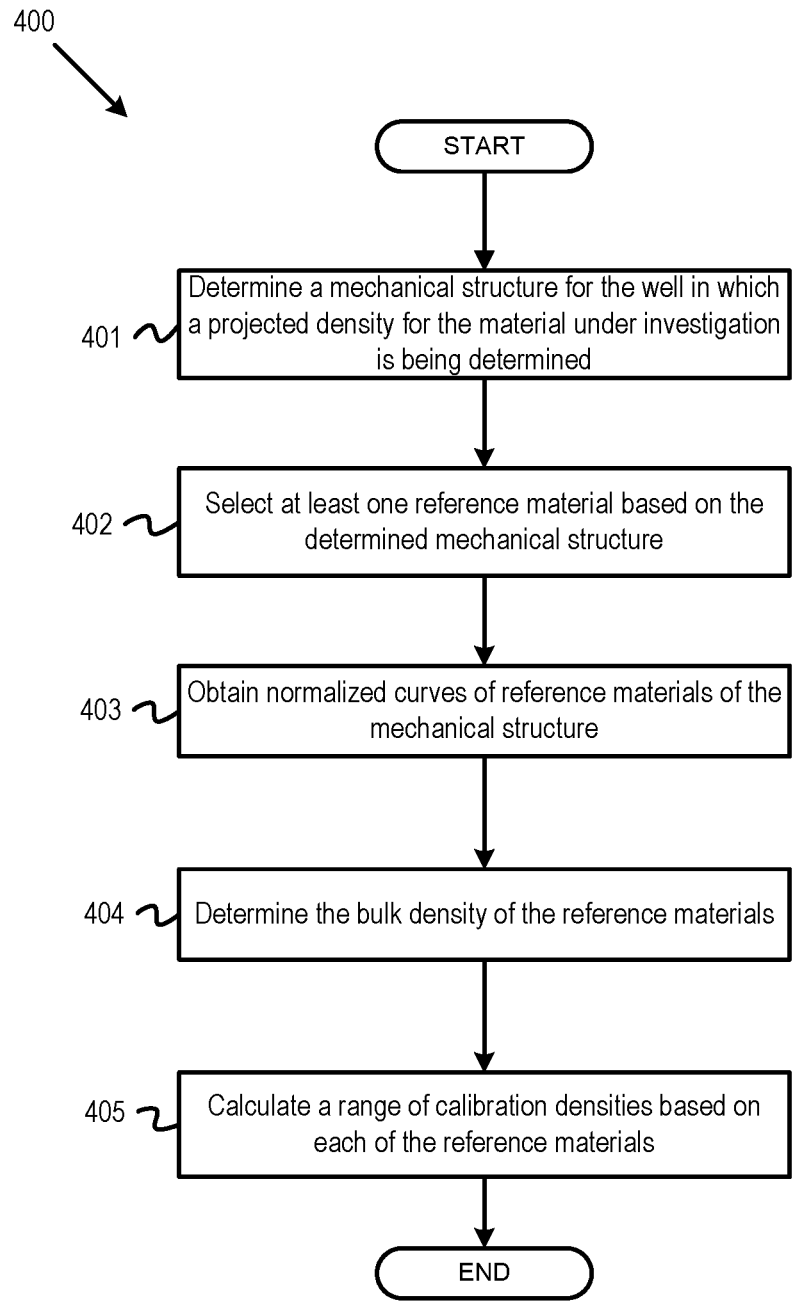
FIG. 4 depicts a flowchart of example operations for calibrating gamma ray measurements for cement density evaluation for a cased wellbore with production tubing installed, according to some embodiments.

At block 305, at least one reference material is selected based on a mechanical structure of the cased wellbore. Example operations for selecting at least one reference material based on the mechanical structure of the cased wellbore are depicted in FIG. 4 (which is described in more detail below).

At block 306, calibration parameters for density calculations are determined based on a reference material of a casing and a reference test material behind the casing. For example, with reference to FIG. 1, a processor in the density tool 112 and/or a processor at surface of the wellbore can determine these calibration parameters. Example operations for determining calibration parameters based on such reference materials are depicted in FIG. 4 (which is described in more detail below).

Figure 5:
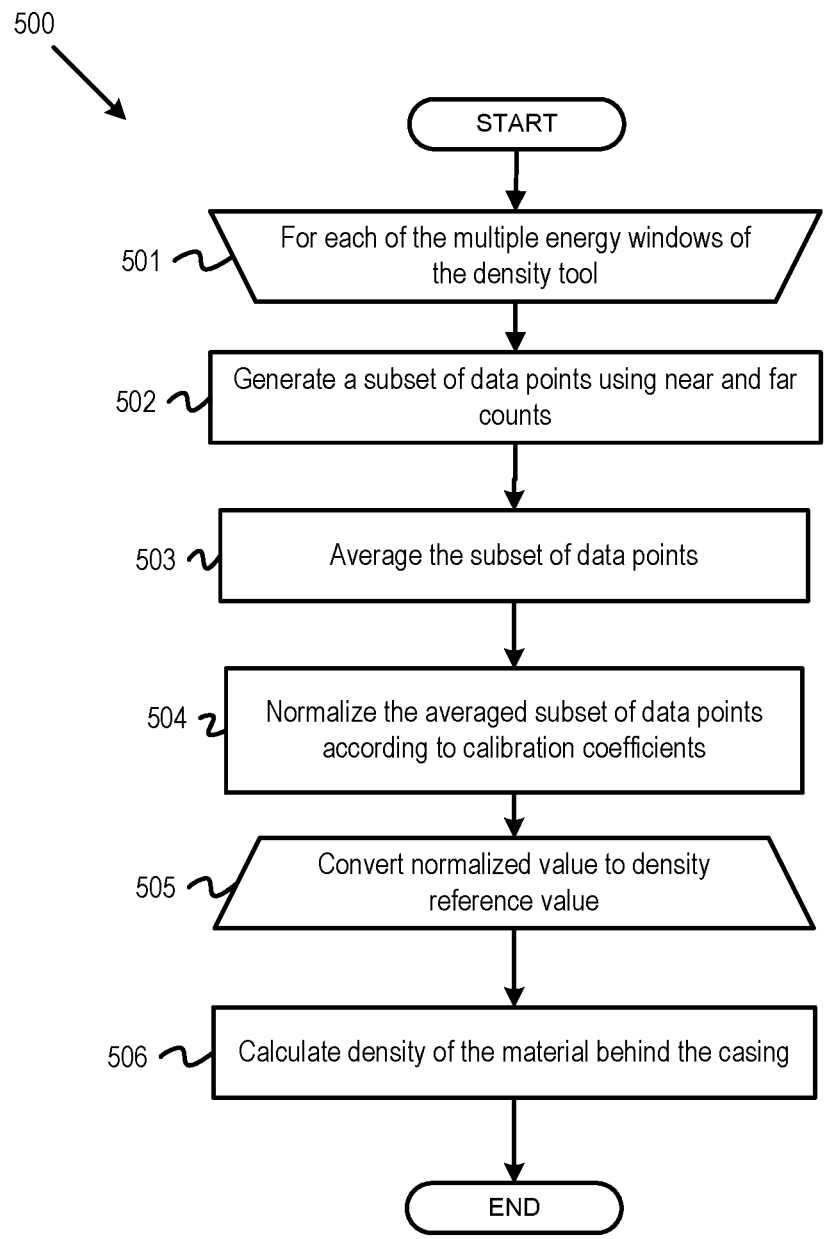
FIG. 5 depicts a flowchart of example operations for cement density calculations for a cased wellbore with production tubing installed, according to some embodiments.

At block 307, a projected density is determined for the material under investigation using the calibration parameter and the detected gamma rays. For example, with reference to FIG. 1, a processor in the density tool 112 and/or a processor at surface of the wellbore can determine the projected density. Example operations for determining the projected density of the material under investigation are depicted in FIG. 5 (which is described in more detail below).

At block 308, properties of the material under investigation (e.g., cement) are determined using the projected density. For example, with reference to FIG. 1, a processor in the density tool 112 and/or a processor at surface of the wellbore can determine properties of the material under investigation. The projected bulk density can provide an indication of contrast in the cement layer. A projected density that varies from the known density of material under investigation indicates that the material may be changing. Changing material properties, which may include air and/or fluid gaps for cement, may indicate deterioration and/or weakness in the material. Identifying such deficiencies in the material can provide preventative diagnosis that can be used for well planning and operations. For example, if a difference between a projected density of the cement and its known density of more than X % (e.g., 5%, 10%, etc.), the cement may be at a first level of deterioration. If the difference is more than Y % (e.g., 20%, 25%, etc.), the cement may be at a second level of deterioration, etc. If the different is less than Z % (1%, 2%, etc.), the deterioration may be essentially nonexistent.

Example operations of selecting at least one reference material based on the mechanical structure of the cased wellbore and determining calibration parameters for a density calculation (i.e., example operations at block 305 and 306 of FIG. 3) are now described. In particular, FIG. 4 depicts a flowchart of example operations for calibrating gamma ray measurements for cement density evaluation for a cased wellbore with production tubing installed, according to some embodiments. Operations of a flowchart 400 are described in reference to the system 100 of FIG. 1. Operations of the flowchart 400 can be performed by hardware, software, firmware, or a combination thereof. Operations of the flowchart 400 begin at block 401.

At block 401, the mechanical structure is determined for the well in which a projected density for the material under investigation is being determined. For example, with reference to FIG. 1, the mechanical structure for the system 100 is determined. In order to determine the reference materials best suited for this analysis, a same or similar mechanical structure of the well under analysis should be used in the calibration. For example, assume that the well under analysis includes a production tubing composed of steel having a defined thickness within a casing also composed of steel and having a defined thickness. Additionally, the mechanical structure can be defined in terms of the composition and thickness of the material under investigation. For example, the material under investigation can be cement having a defined composition and defined thickness. In another example, assume that the mechanical structure is a multi-string-based structure that includes steel+cement+steel+cement+steel+material under investigation. In this case, the casing fixture for calibration should replicate this structure using a mechanical structure represented by steel+cement+steel+cement+steel+reference material behind the casing. The casing fixture for calibration may be an experimentally constructed casing fixture. The casing fixture for calibration may also be the same wellbore that is under analysis. In this situation, a location of the wellbore comprised solely of the reference materials can be analyzed.

At block 402, at least one reference material is selected based on the determined mechanical structure of the well. For example, with reference to FIG. 1, a processor in the density tool 112 and/or a processor at surface of the wellbore can make this selection. In some embodiments, two reference materials can be selected. One reference material can be selected to have a density that is less than or equal to the density of the material under investigation. A second reference material can be selected to have a density greater than or equal to the material under investigation. For example, if the material under investigation is cement, air might be selected as the lighter reference material and a resin cement of known density may be selected as the heavier reference material. Alternatively, water may be selected as the lighter reference material and a metal, such as steel, may be used as the heavier reference material. The reference materials are not limited to the examples provided. Any material with a known density lighter than the material under investigation may be selected as the lighter reference materials and any material with a known density heavier than the material under investigation may be selected as the heavier reference material.

At block 403, normalized curves are obtained for reference materials of the mechanical structure. For example, with reference to FIG. 1, a processor in the density tool 112 and/or a processor at surface of the wellbore can obtain the normalize curves. For example, to obtain normalized curves, two experimental scenarios can be set up: one for each reference material. For each experimental scenario, nuclear radiation (e.g., neutrons) are emitted into the experimentally constructed casing fixture and gamma ray counts can be obtained corresponding to one of the reference materials. Each scenario can have counts corresponding to detection by a near and a far detector of the density tool. The counts can be plotted as a normalized curve to determine the relative variation of energies for each reference material. Thus, there can be four normalized curves in total: 1) counts for the near detector using the lighter material, 2) counts for the far detector using the lighter material, 3) counts for the near detector using the heavier material, and 4) counts using the far detector for the heavier material.

At block 404, the bulk density of the reference materials is determined. For example, with reference to FIG. 1, a processor in the density tool 112 and/or a processor at surface of the wellbore can make this determination. For example, the bulk densities of the reference materials can be determined based on known density values of the selected materials. The reference density for the lighter material (ref$_{dens\_min}$) is given by Equation (1):

$ref_{dens_{min}}$=bulk density of the lighter material.  (1)

The reference density for the heavier material ($ref_{dens\_max}$) is given by Equation (2):

$ref_{dens_{min}}$=bulk density of the heavier material.  (2)

At block 405, the reference formation density is calculated based on each of the reference materials. For example, with reference to FIG. 1, a processor in the density tool 112 and/or a processor at surface of the wellbore can make this calculation. For example, a range of calibration densities can be determined using the counts from the normalized curves obtained at block 403. The peak of the normalized curve can provide the average of the counts for each detector for the lighter and heavier materials. Knowing the averages, the minimum value for the range of calibration densities ($ref_{form\_min}$) can be determined using Equation (3):

$$ref_{form_{min}} = \sqrt{counts_{near_{light}}} - \sqrt{counts_{far_{light}}} \quad (3)$$

where $counts_{near\_light}$ are the average counts for the lighter material measured by the near detector and $counts_{far\_light}$ are the average counts for the lighter material measured by the far detector. Similarly, the maximum value for the range of calibration densities ($ref_{form\_max}$) can be determined using Equation (4):

$$ref_{form_{max}} = \sqrt{counts_{near_{heavy}}} - \sqrt{counts_{far_{heavy}}} \quad (4)$$

where $counts_{near\_heavy}$ are the average counts for the heavier material measured by the near detector and $counts_{far\_heavy}$ are the average counts for the heavier material measured by the far detector. Thus, using the reference materials, these values provide a range of calibration values between which density the material under investigation should fall.

Example operations for determining the projected density of the material under investigation (i.e., example operations at block 306 of FIG. 3) are now described. In particular, FIG. 5 depicts a flowchart of example operations for cement density calculations for a cased wellbore with production tubing installed, according to some embodiments. Operations of a flowchart 500 are described in reference to the system 100 of FIG. 1. Operations of the flowchart 500 can be performed by hardware, software, firmware, or a combination thereof. Operations of the flowchart 500 begin at block 501.

At block 501, individual analysis of data for each raw energy window of the density tool begins. For example, with reference to FIG. 1, a processor in the density tool 112 and/or a computer at the surface of the wellbore 102 can initiate analysis. Operations of blocks 502-505 can be performed individually for each pair of corresponding near and far raw energy windows of the density tool. A typical density tool may include a number of raw energy windows. For example, a density tool may contain four energy windows. In this example, operations of blocks 502-505 would be performed four times, once for each of the four energy windows. While examples refer to four raw energy windows, example embodiments can include a lesser or greater number of energy windows.

At block 502, a subset of data points is generated using counts from the near and far detectors for multiple samples. For example, with reference to FIG. 1, a processor in the density tool 112 and/or a computer at the surface of the wellbore 102 can generate this subset of data points based on the counts detected by the near and far detectors 116A-116D. To obtain results of statistical significance, multiple samples throughout the wellbore can be analyzed. These samples may include measurements taken at different times and/or with the density tool 112 at different positions vertically within the wellbore 102. As an example, one thousand samples may be used. For each sample, the counts of one of the raw energy windows of each of the detectors can be used to generate a subset of points representative of the count rate for each energy window. The subset of points for each sample, $n_{new}$, can be determined using Equation (5):

$$n_{new} = \sqrt{counts_{near}} - \sqrt{counts_{far}} \quad (5)$$

where $counts_{near}$ is the total number of counts for each sample detected by the near detector, and $counts_{far}$ is the total number of counts for each sample detected by the far detector.

At block 503, an average of the subsets of data points is determined. For example, with reference to FIG. 1, a processor in the density tool 112 and/or a processor at surface of the wellbore can make this determination. The average can be determined for the energy window to get a single number count rate for the energy window. The average of the multiple subsets of each sample, $n_{new}$, can be taken over the total number of counts detected by the window.

At block 504, the averaged subset of data points is normalized according to the calibration coefficients. For example, with reference to FIG. 1, a processor in the density tool 112 and/or a processor at surface of the wellbore can perform this normalization. Normalizing the averaged subset of data points adjusts the values from each energy window to a comparable scale, which allows for comparison of the normalized values for different data sets. The averaged subset of data can be normalized according to calibration coefficients of a reference material that is of lower density and a reference material that is of higher density than the cement under investigation. The normalized value, n', which represents the contrast between the cement under investigation and pure cement, can be determined using Equation (6):

$$n' = \frac{n_{new} - ref_{form_{min}}}{ref_{form_{max}}} \quad (6)$$

where n' is the normalized value of the subset of points for the energy window and $ref_{form\_min}$ and $ref_{form\_max}$ are reference numbers determined by the calibration process described in FIG. 4. The energy dependent density value can be used to extract the contrast between the cement under investigation and a sample of pure cement. Due to air pockets and fluid displacement in the cement under investigation, the cement may have defects that impact the detection of gamma rays at each energy window which will vary from window to window.

At block 505, the normalized value of the subset of points for the energy window is converted to a density reference value for the energy window. For example, with reference to FIG. 1, a processor in the density tool 112 and/or a processor at surface of the wellbore can perform this conversion. Because each window represents a different range of energies, some of which are more susceptible to the photoelectric effect or the electron density of the material, the density values determined from each energy window will vary according to the energy. Typically, lower energy windows are more susceptible to the photoelectric effect with higher energy windows are more susceptible to the electron density. The density reference value represents the energy dependent density determined for a set energy range corresponding to the energy window. The density reference value can be determined using Equation (7):

$$n''=\#n'*ref_{dens_{max}}+ref_{dens_{min}} \quad (7)$$

where n" is the density reference value for the formation for the energy window and $ref_{dens\_max}$ and $ref_{dens\_min}$ are the bulk density of a heavier and lighter reference material, respectively, as described in FIG. 4.

At block 506, the density of the material behind the casing is calculated. For example, with reference to FIG. 1, a processor in the density tool 112 and/or a processor at surface of the wellbore can make this calculation. After determination of the density reference value for each of the energy windows, a projected density of the cement can be determined. The projected density value represents the projected density of the material under investigation based on samples and energy windows used during operation. The projected density of the cement under investigation can be determined using Equation (8):

$$\rho_{projected} = \frac{1}{n_i}\left(\sum_i n_i''\right) \quad (8)$$

where $\rho_{projected}$ is the projected density of the material behind the casing, and i is the number of the raw energy window in order from lowest energy to highest energy. By combining multiple samples over multiple energy windows, a representative density of the cement can be determined. This projected density can be used to evaluate the characteristics of the material under investigation.

FIGS. 3, 4, and 5 are annotated with a series of numbers. These numbers represent stages of operations. Although these stages are ordered for this example, the stages illustrate one example to aid in understanding this disclosure and should not be used to limit the claims. Subject matter falling within the scope of the claims can vary with respect to the order and some of the operations.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general-purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain or store a program for use by or in connection with an instruction execution system, apparatus, or device. A machine-readable storage medium is not a machine-readable signal medium.

A machine-readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

The program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks.

Example Computer

Figure 6:
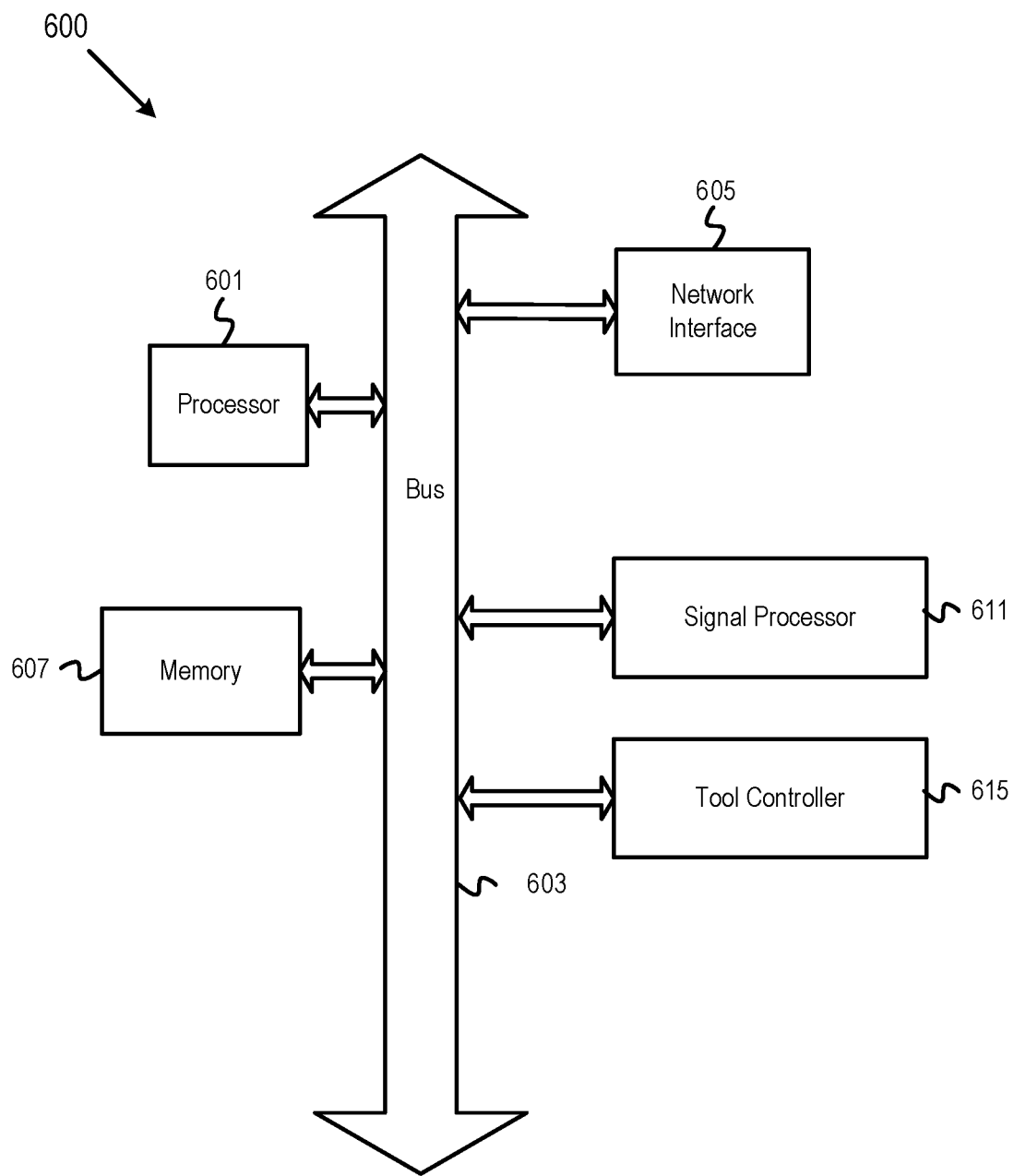
FIG. 6 depicts an example computer, according to some embodiments.

FIG. 6 depicts an example computer, according to some embodiments. A computer 600 includes a processor 601 (possibly including multiple processors, multiple cores, multiple nodes, and/or implementing multi-threading, etc.). The computer 600 includes a memory 607. The memory 607 may be system memory or any one or more of the above already described possible realizations of machine-readable media. The computer 600 also includes a bus 603 and a network interface 605.

The system also includes a signal processor 611. The signal processor 611 may perform operations of FIG. 5. The system also includes a tool controller 615. the tool calibrator 615 may perform operations of FIGS. 3-4. Any one of the previously described functionalities may be partially (or entirely) implemented in hardware and/or on the processor 601. For example, the functionality may be implemented with an application specific integrated circuit, in logic implemented in the processor 601, in a co-processor on a peripheral device or card, etc. Further, realizations may include fewer or additional components not illustrated in FIG. 6 (e.g., video cards, audio cards, additional network interfaces, peripheral devices, etc.). The processor 601 and the network interface 605 are coupled to the bus 603. Although illustrated as being coupled to the bus 603, the memory 607 may be coupled to the processor 601.

While the aspects of the disclosure are described with reference to various implementations and exploitations, it will be understood that these aspects are illustrative and that the scope of the claims is not limited to them. In general, techniques for cased-hole density calculations as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

Example Embodiments

A method comprises detecting, by at least one detector positioned within a casing of a wellbore that includes a sealing material positioned between the casing and a subsurface formation in which the wellbore is formed, electromagnetic radiation generated in response to nuclear radiation being emitted outward toward the subsurface formation. The method comprises determining an electromagnetic radiation count based on the detected electromagnetic radiation, selecting at least one of a first reference material having a density that is less than a density of the sealing material and a second reference material having a density that is greater than the density of the sealing material, adjusting the electromagnetic radiation count based on the density of the at least one of the first reference material and the second reference material, and determining a density of the sealing material based on the adjusted electromagnetic radiation count.

Detecting the electromagnetic radiation comprises detecting gamma rays.

The method further comprises emitting, from a radiation source located within the casing of the wellbore, the nuclear radiation outward toward the subsurface formation. The at least one detector and the radiation source are located within a tubing positioned in the casing of the wellbore.

The sealing material comprises cement.

The method further comprises identifying deficiencies in the sealing material based on the density of the sealing material.

The at least one detector comprises a near detector and a far detector that are located within a tubing positioned in the casing of the wellbore. Detecting of the electromagnetic radiation comprises detecting, by the near detector within at least two energy windows, a near electromagnetic radiation and detecting, by the far detector within the at least two energy windows, a far electromagnetic radiation. Determining the electromagnetic radiation count comprises determining a near electromagnetic radiation count at the at least two energy windows based on the detected near electromagnetic radiation and determining a far electromagnetic radiation count at the at least two energy windows based on the detected far electromagnetic radiation. Adjusting the electromagnetic radiation count comprises adjusting the near electromagnetic radiation count and the far electromagnetic radiation count based on the density of the at least one of the first reference material and the second reference material. Determining the density of the sealing material comprises determining the density of the sealing material based on the adjusted near electromagnetic radiation count and the adjusted far electromagnetic radiation count.

A system comprises a radiation source to be positioned within a production tubing located in a casing of a wellbore that includes a sealing material positioned between the casing and a subsurface formation in which the wellbore is formed. The radiation source is to emit nuclear radiation outward toward the subsurface formation. A near detector is to be positioned within the production tubing at a first distance from the radiation source. The near detector is to detect, within at least two energy windows, gamma rays generated in response to the nuclear radiation being emitted by the radiation source. A far detector is to be positioned within the production tubing at a second distance from the radiation source. The far detector is to detect, within the at least two energy windows, gamma rays generated in response to the nuclear radiation being emitted by the radiation source. The system comprises a processor and a computer-readable medium having instructions stored thereon that are executable by the processor to cause the system to determine a near gamma ray count based on the detected gamma rays by the near detector, determine a far gamma ray count based on the detected gamma rays by the far detector, select a first reference material having a density that is less than a density of the sealing material, select a second reference material having a density that is greater than the density of the sealing material, adjust the near gamma ray count and the far gamma ray count based on the density of the first reference material and the density of the second reference material, and determine a density of the sealing material based on the adjusted near gamma ray count and the adjusted far gamma ray count.

The sealing material comprises a cement.

The computer-readable medium comprises instructions executable by the processor to cause the system to identify deficiencies in the sealing material based on the density of the sealing material.

The at least two energy windows comprise a first energy window sensitive to a photoelectric effect and a second energy window sensitive to an electron density of the sealing material.

The instructions to cause the system to adjust the near gamma ray count and the far gamma ray count comprise instructions to cause the system to, for each energy window, generate a subset of data points using the near gamma ray count and the far gamma ray count, average the subset of data points according to a total number of gamma ray counts detected by the near detector and the far detector, normalize the averaged subset of data points according to the density of the first reference material and the density of the second reference material, and convert the normalized average subset of data points to a density reference value.

A non-transitory, computer-readable medium has instructions stored thereon that are executable by a processor to perform operations comprising determining an electromagnetic radiation count based on an electromagnetic radiation detected by at least one detector positioned within a casing of a wellbore that includes a sealing material positioned between the casing and a subsurface formation in which the wellbore is formed. The electromagnetic radiation is generated in response to nuclear radiation being emitted outward toward the subsurface formation from a source positioned within the casing. The operations comprise selecting at least one of a first reference material having a density that is less than a density of the sealing material and a second reference material having a density that is greater than the density of the sealing material, adjusting the electromagnetic radiation count based on the density of the at least one of the first reference material and the second reference material, and determining a density of the sealing material based on the adjusted electromagnetic radiation count.

The electromagnetic radiation comprises gamma rays.

The at least one detector and the source are located within a tubing positioned in the casing of the wellbore.

The sealing material comprises cement.

The instructions to cause the processor to perform operations comprising adjusting the electromagnetic radiation count based on the density of the at least one of the first reference material and the second reference material comprise instructions to cause the processor perform operations comprising, for each energy window, generating a subset of data points based on the electromagnetic radiation count, averaging the subset of data points according to a total number of electromagnetic radiation counts detected by the at least one detector, normalizing the averaged subset of data points according to the density of the first reference material and the density of the second reference material, and converting the normalized average subset of data points to a density reference value.

The instructions further comprise instructions stored thereon that are executable by a processor to perform operations comprising identifying deficiencies in the sealing material based on the density of the sealing material.

The at least one detector comprises a near detector and a far detector that located within a tubing positioned in the casing of the wellbore. Detecting of the electromagnetic radiation comprises detecting, by the near detector within at least two energy windows, a near electromagnetic radiation and detecting, by the far detector within the at least two energy windows, a far electromagnetic radiation. Determining the electromagnetic radiation count comprises determining a near electromagnetic radiation count at the at least two energy windows based on the detected near electromagnetic radiation and determining a far electromagnetic radiation count at the at least two energy windows based on the detected far electromagnetic radiation. Adjusting the electromagnetic radiation count comprises adjusting the near electromagnetic radiation count and the far electromagnetic radiation count based on the density of the at least one of the first reference material and the second reference material. Determining the density of the sealing material comprises determining the density of the sealing material based on the adjusted near electromagnetic radiation count and the adjusted far electromagnetic radiation count.

The electromagnetic radiation is detected within at least two energy windows. The at least two energy windows comprise a first energy window sensitive to a photoelectric effect and a second energy window sensitive to an electron density of the sealing material.

The invention claimed is:

1. A method comprising:
   detecting, by at least one detector positioned within a casing of a wellbore that includes a sealing material positioned between the casing and a subsurface formation in which the wellbore is formed, electromagnetic radiation generated in response to nuclear radiation being emitted outward toward the subsurface formation;
   determining an electromagnetic radiation count based on the detected electromagnetic radiation;
   selecting at least one of a first reference material having a density that is less than a density of the sealing material and a second reference material having a density that is greater than the density of the sealing material;
   adjusting the electromagnetic radiation count based on the density of the at least one of the first reference material and the second reference material; and
   determining a projected density of the sealing material based on the adjusted electromagnetic radiation count.

2. The method of claim 1, wherein detecting the electromagnetic radiation comprises detecting gamma rays.

3. The method of claim 1, wherein the sealing material comprises cement.

4. The method of claim 1, further comprising:
   identifying deficiencies in the sealing material based on the density of the sealing material.

5. The method of claim 1,
   wherein the at least one detector comprises a near detector and a far detector;
   wherein detecting of the electromagnetic radiation comprises,
      detecting, by the near detector within at least two energy windows, a near electromagnetic radiation, and
      detecting, by the far detector within the at least two energy windows, a far electromagnetic radiation;
   wherein determining the electromagnetic radiation count comprises,
      determining a near electromagnetic radiation count at the at least two energy windows based on the detected near electromagnetic radiation, and
      determining a far electromagnetic radiation count at the at least two energy windows based on the detected far electromagnetic radiation;
   wherein adjusting the electromagnetic radiation count comprises,
      adjusting the near electromagnetic radiation count and the far electromagnetic radiation count based on the density of the at least one of the first reference material and the second reference material; and
   wherein determining the projected density of the sealing material comprises,
      determining the projected density of the sealing material based on the adjusted near electromagnetic radiation count and the adjusted far electromagnetic radiation count.

6. The method of claim 1, wherein adjusting the electromagnetic radiation count based on the density of the at least one of the first reference material and the second reference material comprises, for each energy window:
   generating a subset of data points based on the electromagnetic radiation count;

averaging the subset of data points according to a total number of electromagnetic radiation counts detected by the at least one detector;

normalizing the averaged subset of data points according to the density of the first reference material and the density of the second reference material; and converting the normalized average subset of data points to a density reference value.

7. The method of claim 1, wherein the electromagnetic radiation is detected within at least two energy windows, wherein the at least two energy windows comprise a first energy window sensitive to a photoelectric effect and a second energy window sensitive to an electron density of the sealing material.

8. The method of claim 1, further comprising:
emitting, from a radiation source located within the casing of the wellbore, the nuclear radiation outward toward the subsurface formation.

9. The method of claim 8, wherein the at least one detector and the radiation source are located within a tubing positioned in the casing of the wellbore.

10. A system comprising:
at least one detector positioned within a casing of a wellbore that includes a sealing material positioned between the casing and a subsurface formation in which the wellbore is formed, the at least one detector configured to detect electromagnetic radiation generated in response to nuclear radiation being emitted outward toward the subsurface formation;

a processor; and a computer-readable medium having instructions stored thereon that are executable by the processor to cause the system to:
determine an electromagnetic radiation count based on the detected electromagnetic radiation;
select at least one of a first reference material having a density that is less than a density of the sealing material and a second reference material having a density that is greater than the density of the sealing material;
adjust the electromagnetic radiation count based on the density of the at least one of the first reference material and the second reference material; and
determine a projected density of the sealing material based on the adjusted electromagnetic radiation count.

11. The system of claim 10, wherein the at least one detector configured to detect the electromagnetic radiation includes the at least one detector configured to detect gamma rays.

12. The system of claim 10, wherein the sealing material comprises cement.

13. The system of claim 10, wherein the computer-readable medium comprises instructions executable by the processor to cause the system to:
identify deficiencies in the sealing material based on the density of the sealing material.

14. The system of claim 10, wherein the at least one detector comprises a near detector and a far detector, further comprising:
the near detector configured to detect a near electromagnetic radiation within at least two energy windows; and
the far detector configured to detect a far electromagnetic radiation within the at least two energy windows;

wherein the instructions executable by the processor to cause the system to determine the electromagnetic radiation count comprises instructions executable by the processor to cause the system to,
determine a near electromagnetic radiation count at the at least two energy windows based on the detected near electromagnetic radiation, and
determine a far electromagnetic radiation count at the at least two energy windows based on the detected far electromagnetic radiation;

wherein the instructions executable by the processor to cause the system to adjust the electromagnetic radiation count comprises instructions executable by the processor to cause the system to,
adjust the near electromagnetic radiation count and the far electromagnetic radiation count based on the density of the at least one of the first reference material and the second reference material; and wherein the instructions executable by the processor to cause the system to determine the projected density of the sealing material comprises instructions executable by the processor to cause the system to,
determine the projected density of the sealing material based on the adjusted near electromagnetic radiation count and the adjusted far electromagnetic radiation count.

15. The system of claim 10, wherein the instructions executable by the processor to cause the system to adjust the electromagnetic radiation count based on the density of the at least one of the first reference material and the second reference material comprises, for each energy window, instructions executable by the processor to cause the system to:
generate a subset of data points based on the electromagnetic radiation count;
average the subset of data points according to a total number of electromagnetic radiation counts detected by the at least one detector;
normalize the averaged subset of data points according to the density of the first reference material and the density of the second reference material; and
convert the normalized average subset of data points to a density reference value.

16. The system of claim 10, wherein the electromagnetic radiation is detected within at least two energy windows, wherein the at least two energy windows comprise a first energy window sensitive to a photoelectric effect and a second energy window sensitive to an electron density of the sealing material.

17. The system of claim 10, further comprising:
a radiation source located within the casing of the wellbore, the radiation source configured to emit the nuclear radiation outward toward the subsurface formation.

18. The system of claim 17, wherein the at least one detector and the radiation source are located within a tubing positioned in the casing of the wellbore.

* * * * *